US012708777B2

(12) United States Patent
Eggen et al.

(10) Patent No.: US 12,708,777 B2
(45) Date of Patent: Aug. 18, 2026

(54) INTEGRATED CARDIOVERTER DEFIBRILLATOR-MUSCLE STIMULATOR FOR CARDIOMYOPLASTY

(71) Applicant: Medtronic, Inc., Minneapolis, MN (US)

(72) Inventors: Michael D. Eggen, Chisago City, MN (US); Sean R. Farrell, Maple Grove, MN (US); Zhongping Yang, Woodbury, MN (US); Richard J. O'Brien, Hugo, MN (US); Yong K. Cho, Excelsior, MN (US)

(73) Assignee: Medtronic, Inc., Minneapolis, MN (US)

( * ) Notice: Subject to any disclaimer, the term of this patent is extended or adjusted under 35 U.S.C. 154(b) by 326 days.

(21) Appl. No.: 18/225,884

(22) Filed: Jul. 25, 2023

(65) Prior Publication Data

US 2024/0066306 A1 Feb. 29, 2024

Related U.S. Application Data

(60) Provisional application No. 63/373,635, filed on Aug. 26, 2022.

(51) Int. Cl.

*A61N 1/365* (2006.01)
*A61N 1/362* (2006.01)
*A61N 1/37* (2006.01)

(52) U.S. Cl.

CPC ....... *A61N 1/36514* (2013.01); *A61N 1/3627* (2013.01); *A61N 1/3702* (2013.01)

(58) Field of Classification Search

CPC ........ A61N 1/05; A61N 1/0587; A61N 1/059; A61N 1/362; A61N 1/3621; A61N 1/3622; A61N 1/3625; A61N 1/3627; A61N 1/365; A61N 1/3956

See application file for complete search history.

(56) References Cited

U.S. PATENT DOCUMENTS 5,069,680 A 12/1991 Grandjean
5,195,518 A * 3/1993 Mannion ............ A61M 60/515 607/9
5,251,621 A 10/1993 Collins
5,328,442 A 7/1994 Levine
5,344,386 A 9/1994 Schaldach (Continued)

FOREIGN PATENT DOCUMENTS

WO WO-2010051411 A1 * 5/2010 ........... A61B 5/7217

OTHER PUBLICATIONS

Guldner et al., "Autologous Muscular Treatment Options for Endstage Heart Failure—A Critical Appraisal of the Dynamic Cardiomyoplasty (DCMP) vs. a New Concept of a Closed-Loop Controlled DCMP (CLC-DCMP)", Regenerative Medicine and Tissue Engineering, Intech, May 22, 2013, pp. 795-830, Chapter 32.

*Primary Examiner* — Brian T Gedeon
(74) *Attorney, Agent, or Firm* — Shumaker & Sieffert, P.A.

(57) ABSTRACT

An example implantable medical device includes a stimulating lead includes receive one or more signals indicative of one or more physiologic parameters; deliver electrical therapy to stimulate a muscle wrapped around a heart via one or more electrodes of a stimulating lead; and adjust an amount of the electrical therapy delivered, via the stimulating electrodes, based on the one or more physiologic parameters.

19 Claims, 5 Drawing Sheets

(56) References Cited

U.S. PATENT DOCUMENTS

| | | | | |
|---|---|---|---|---|
| 5,607,385 | A | 3/1997 | Francischelli et al. | |
| 5,693,000 | A | 12/1997 | Crosby et al. | |
| 5,807,234 | A | 9/1998 | Bui et al. | |
| 10,952,681 | B2 | 3/2021 | Sharma et al. | |
| 2009/0234406 | A1* | 9/2009 | Shuros | A61N 1/3629 607/11 |
| 2010/0179608 | A1* | 7/2010 | Limousin | A61N 1/3627 607/18 |
| 2012/0253207 | A1 | 10/2012 | Sarkar et al. | |

* cited by examiner

INTEGRATED CARDIOVERTER DEFIBRILLATOR-MUSCLE STIMULATOR FOR CARDIOMYOPLASTY

RELATED APPLICATIONS

This application claims the benefit of U.S. Provisional Application Ser. No. 63/373,635, filed Aug. 26, 2022, the entire contents of each of which are incorporated herein by reference.

TECHNICAL FIELD

The present application relates to cardiac therapy and, more particularly, to devices and techniques for cardiomyoplasty.

BACKGROUND

Severe chronic cardiac insufficiency arising from cardiac disease or injury shortens and degrades the quality of life of many patients. One form of severe chronic cardiac insufficiency, congestive heart failure, is a pathophysiological state in which cardiac output is inadequate to meet physiological requirements of the body. The mortality rate for congestive heart failure is greater than 50% within 5 years of onset. Treatments for severe chronic cardiac insufficiency include heart transplants, artificial heart implants, and cardiomyoplasty. Cardiac transplantation, using cyclosporine to inhibit tissue rejection, is a very successful technique for prolonging a cardiac patient's life, improving the survival rate to 80% at 1 year. However, the transplant operation is very expensive and heart availability is limited. The artificial heart has had very limited success.

Dynamic cardiomyoplasty is a therapy for class III/IV heart failure patients in which the latissimus dorsi (LD) or other skeletal muscle is surgically wrapped around the heart and stimulated in concert with myocardial contractions in order to increase the pump function of the heart. Dynamic cardiomyoplasty is a surgical and electrical therapeutic technique in which a skeletal muscle flap is dissected from a patient, while maintaining its innervating neural tissues and neurovascular structures, and surgically placed around the patient's heart.

In first implementations of this therapy, the stimulation was triggered by the intrinsic R-wave and there was no physiological feedback to the stimulator. An electrical stimulation device with an electrical pulse generator and intramuscular electrodes is implanted which performs muscle electrical stimulation in synchrony with ventricular systole to support cardiac pumping.

SUMMARY

The patient population that undergoes dynamic cardiomyoplasty has had a high prevalence of sudden cardiac arrest (SCA). However, it may be considered too invasive to implant two devices (a stimulator for the LD and an implantable cardioverter defibrillator (ICD)). In addition, patients that undergo past examples of dynamic cardiomyoplasty have dealt with overstimulation of the LD muscle that may lead to fatigue of the LD muscle and/or may negatively remodel the LD muscle fibers, which may lead to adverse health events of the heart, such as SCA and even death. In some examples, patients who have undergone dynamic cardiomyoplasty may need to have a device replaced that performs cardiac pacing of the heart and/or long-term stimulation of skeletal muscles.

In accordance with some techniques of the disclosure, an IMD may stimulate the LD muscle enough to remodel the heart and support pump function while not overstimulating the LD muscle to fatigue and negatively remodel the LD muscle fibers in response to receiving physiological parameters. In some examples, IMD may stimulate the LD muscle in combination with providing pacing to the heart and may adjust stimulation of the LD muscle based on pacing being provided to the heart. In some examples, the IMD may be configured both to stimulate the LD and provide antitachyarrhythmia therapy, e.g., shocks, to terminate ventricular tachyarrhythmias, such as ventricular tachyarrhythmias that may result in SCA. In addition, in accordance with some techniques of this disclosure, the implantable medical device may be configured to minimize the invasiveness of a procedure to replace a previous device that performs cardiac pacing of the heart and/or long-term stimulation of skeletal muscles.

In one example, an implantable medical device comprises a stimulating lead comprising one or more electrodes; and circuitry configured to: receive one or more signals indicative of one or more physiologic parameters; deliver electrical therapy to stimulate a muscle wrapped around a heart via one or more electrodes of a stimulating lead; and adjust an amount of the electrical therapy delivered, via the stimulating electrodes, based on the one or more physiologic parameters.

In another example, an implantable medical device comprises a housing; and circuitry within the housing, the circuitry configured to: receive one or more signals indicative of one or more physiologic parameters; and output a signal to cause electrical therapy to be delivered to stimulate a muscle wrapped around a heart based on the one or more physiologic parameters; and an implantable medical lead configured to be coupled to the medical device and to receive the signal output by the circuitry, the implantable medical lead comprising one or more stimulating electrodes to deliver the electrical therapy to stimulate the muscle wrapped around the heart in response to receiving the signal received from the circuitry, wherein the circuitry is configured to send a second signal to adjust an amount of the electrical therapy to be delivered, via the stimulating electrodes, based on the one or more physiologic parameters.

In another example, a method comprises receiving, via circuitry, one or more signals indicative of one or more physiologic parameters; determining, via the circuitry, an amount of electrical therapy to deliver to stimulate a muscle wrapped around a heart of a patient based on the one or more physiologic parameters; and delivering, via a stimulating lead, the determined amount of electrical therapy to stimulate the muscle wrapped around the heart of the patient.

This summary is intended to provide an overview of the subject matter described in this disclosure. It is not intended to provide an exclusive or exhaustive explanation of the systems, devices, and methods described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

As used herein, relational terms, such as "first" and "second," "over" and "under," "front" and "rear," and the like, may be used solely to distinguish one entity or element from another entity or element without necessarily requiring or implying any physical or logical relationship or order between such entities or elements.

Figure 1:
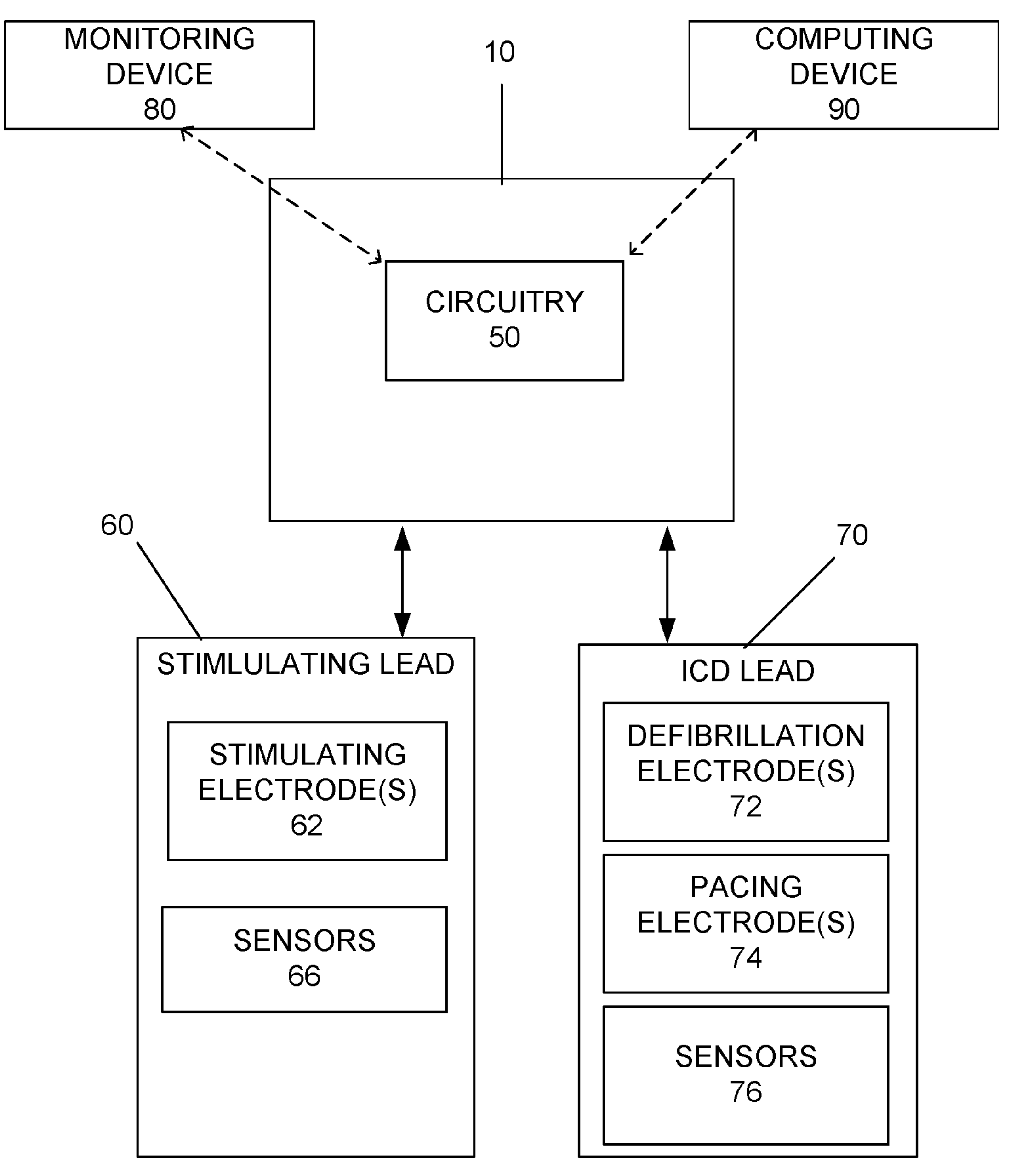
FIG. 1 is a functional block diagram of an example implantable medical device, in accordance with techniques described herein.

FIG. 1 is a functional block diagram of an implantable medical device (IMD) 10 in accordance with the techniques of the disclosure.

In accordance with the techniques of the disclosure, an implantable medical device 10 may adjust stimulation of a wrapped muscle around the heart, such as the LD muscle, based on one or more sensed physiologic parameters, to stimulate the wrapped muscle enough to remodel the heart and support pump function while not overstimulating to fatigue and negatively remodel the wrapped muscle fibers. In some examples, the wrapped muscle may be an abdominal muscle. In some examples, the wrapped muscle may be wrapped around the ascending aorta to create a 5*t* h chamber.

In some examples, implantable medical device 10 may include circuitry 50 and may be coupled to a stimulating lead 60. In some examples, implantable medical device 10 may further be coupled to an implantable cardioverter defibrillator (ICD) lead 70. In some examples, circuitry 50 may be configured to receive one or more signals indicative of one or more physiologic parameters. In some examples, the signals may be received from one or more of sensors 66 of the stimulating lead 60, sensors 76 of the ICD lead 70, a monitoring device 80 separate from the IMD 10, or from an external computing device 90. One example of such a monitoring device 80 is the Reveal LINQ II™ Insertable Cardiac Monitor (ICM), available from Medtronic plc, which may be inserted subcutaneously in the patient. Circuitry 50 may further be configured to deliver electrical therapy to stimulate a muscle wrapped around a heart. In some examples, the muscle wrapped around the heart may be a latissimus dorsi muscle graft.

In some examples, stimulating lead 60 of IMD 10 may include one or more stimulating electrodes 62 to deliver the electrical therapy to stimulate the muscle wrapped around the heart based on the one or more physiologic parameters. In some examples, circuitry 50 may be configured to adjust an amount of the electrical therapy to be delivered, via the stimulating electrodes 62, based on the one or more physiologic parameters.

Stimulating lead 60 of IMD 10 may include one or more stimulating lead sensor(s) 66 to detect and provide signals to circuitry 50 indicative of one or more physiologic parameters of the wrapped muscle. In some examples, stimulating lead sensor(s) 66 may include an accelerometer.

In some examples, circuitry 50 may be configured to determine one or more of an amount of fatigue of the wrapped muscle, strength of the wrapped muscle contractions, activity, tissue perfusion, or posture based on the one or more physiologic parameters sensed by stimulating lead sensor(s) 66. In some examples, circuitry 50 may be configured to determine one or more of an amount of fatigue of the wrapped muscle or strength of the wrapped muscle contractions based on the values sensed by an accelerometer included in the stimulating lead 60. In some examples, stimulating lead sensor(s) 66 may include one or more accelerometers. In some examples, an accelerometer of stimulating lead 60 may be positioned on a surface of the stimulating lead 60.

Stimulating lead sensor(s) 66 may include electrodes, gyroscope(s), accelerometer(s) (e.g., 3-axis accelerometers), optical sensor(s), impedance sensor(s), temperature sensor(s), pressure sensor(s), heart sound sensor(s) (e.g., microphones), chemical sensor(s), and other sensors, and sensing circuitry. In some examples, instead of or in addition to such sensors being included on lead 60, such sensors may be included on ICD lead 70 or on or within IMD 10.

In some examples, ICD lead 70 may include one or more of defibrillation electrode(s) 72, pacing electrode(s) 74, or sensor(s) 76. In some examples, sensor(s) 76 may detect and provide the signals indicative of one or more the physiologic parameters. In some examples, circuitry 50 may be configured to determine one or more of heart failure status, heart failure risk score, myocardial state, or other based on the one or more physiologic parameters sensed by sensor(s) 76.

Sensor(s) 76 may include electrodes, gyroscope(s), accelerometer(s) (e.g., 3-axis accelerometers), optical sensor(s), impedance sensor(s), temperature sensor(s), pressure sensor(s), heart sound sensor(s) (e.g., microphones), chemical sensor(s), and other sensors, and sensing circuitry.

In some examples, circuitry 50 may include a clock to determine time of day. In some examples, circuitry 50 may determine time of day based, at least in part, on a signal received from an external device, such as monitoring device 80 or computing device 90. In some examples, circuitry 50 may determine time of day based, at least in part, on posture determined from signals received from stimulating lead sensor(s) 66.

In some examples, if the wrapped muscle is overfatigued, the wrapped muscle fibers may be negatively remodeled. In some examples, circuitry 50 may be configured to adjust the amount of the electrical therapy to be delivered, via the stimulating electrodes 62, to the wrapped muscle based, at least in part, on the determined amount of fatigue of the wrapped muscle. In some examples, if circuitry 50 determines the wrapped muscle is overfatigued, circuitry 50 may reduce stimulation of the wrapped muscle. In some examples, circuitry 50 may be configured to adjust the amount of the electrical therapy to be delivered based on time of day.

In some examples, physiologic parameters include one or more of heart failure status, heart failure risk score, myocardial state, activity, muscle fatigue, tissue perfusion, contraction strength of the wrapped muscle, respiration, or body posture. In some examples, physiological parameters may further include one or more of heart rate, impedance measurements, impedance scores, fluid indices, respiratory rate, activity data, cardiac electrograms (ECGs), historical physiological data, blood pressure values, posture, chronotropic incompetence, short-term heart rate variability, sleep disordered breathing, oxygen saturation, glucose level, stress hormone level, heart sounds, body motion, R-wave morphology, R-wave amplitude, etc.

In some examples, heart failure risk score may be derived from one or more of the physiological parameters as described in the publications incorporated by reference discussed below. Tissue perfusion may be a measure of the oxygen within the capillary bed, such as from an optical sensor. A high and stable tissue oxygen would indicate adequate perfusion, i.e., an indication of how well the cardiomyoplasty is working. Contraction strength may be derived from an impedance signal from a lead electrode, such as from a rate of change of impedance during the contraction. In some examples, contraction strength may be derived from an accelerometer on a lead. Respiration may be derived from an ECG or electrodes on the IMD 10 to measure thoracic muscle contractions. Posture may be derived from an accelerometer.

In some examples, circuitry 50 may be configured to adjust the amount of electrical therapy to be provided by stimulating electrode(s) 62 to increase stimulation of the wrapped muscle above an overdrive threshold in response to determining atrial fibrillation, ventricular fibrillation or ventricular tachycardia occurred based, at least in part, on the one or more physiologic parameters. For example, circuitry 50 may determine one or more of atrial fibrillation, ventricular fibrillation or ventricular tachycardia occurred in the heart based on parameters sensed by one or more of sensor(s) 76, stimulating lead sensor(s) 66. In some examples, circuitry 50 may determine one or more of atrial fibrillation, ventricular fibrillation or ventricular tachycardia occurred in the heart based on parameters received from monitoring device 80 or external computing device 90. In some examples, circuitry 50 may determine one or more of atrial fibrillation, ventricular fibrillation or ventricular tachycardia occurred in the heart based on parameters received from one or more of stimulating lead 60, ICD lead 70, monitoring device 80 or external computing device 90.

In some examples, when activity of a patient increases due to exercise, additional muscle contraction may be needed. In some examples, circuitry 50 may be configured to adjust an amount of electrical therapy to be delivered via stimulating electrode(s) 62 to increase stimulation, such as increasing pacing rate, of the wrapped muscle in response to determining a level of activity is above a threshold value based, at least in part, on the one or more physiologic parameters.

In some examples, when a patient has a heart failure status that is below a threshold, which shows the heart is in a good condition, stimulation of the wrapped muscle may be reduced to preserve the wrapped muscle. In some examples, decreasing stimulation may include one or more of reducing a number of stimulation pulses (e.g., reducing pacing rate) or reducing a strength of stimulation pulses to be delivered. In some examples, circuitry 50 may be configured to adjust the amount of electrical therapy to decrease stimulation of the wrapped muscle in response to determining heart failure status is below a threshold value based, at least in part, on the one or more physiologic parameters.

Some examples of determining heart failure status and/or heart failure risk status are described in U.S. Publication No. 2012/0253207 A1, entitled "Heart Failure Monitoring," by Sarkar et al., which is incorporated herein by reference in its entirety.

In addition, some examples of differentiating heart failure status and/or heart failure risk statuses in a device are described in commonly-assigned U.S. application Ser. No. 16/119,329 by Sharma et al., entitled "DIFFERENTIATION OF HEART FAILURE RISK SCORES FOR HEART FAILURE MONITORING," filed on Aug. 31, 2018, incorporated herein by reference in its entirety. In this example, the IMD may provide diagnostic information to one or more devices, such as IMD programmers or other computing devices. The diagnostic information may be related to, generated from, or may even include the one or more patient metrics. The diagnostic information may include, as examples, values of the patient metrics and raw data used to derive the values of the patient metrics. The patient metrics may include, as examples, therapy use statistics (e.g., pacing or shocks), thoracic impedance, heart rate, heart rate variability, patient activity, and a percentage of time receiving cardiac resynchronization therapy. Other example patient metrics include weight, blood pressure, respiration rate, sleep apnea burden (which may be derived from respiration rate), temperature, ischemia burden, the occurrence, frequency or duration cardiac events, and sensed cardiac intervals (e.g., heart rate or Q-T intervals).

For example, an external monitoring device, such as a server or other computing device, acquires and utilizes the patient metrics associated with diagnostic information from the IMD, and uses the patient metrics to generate heart failure risk scores and differentiate between heart failure risk status alerts. The scheme of alerts described herein applies to all types of risk segmentations. Heart failure risk statuses may be segmented by drawing cut-offs on numeric scores. Default cut-offs for Low, Medium, High statuses may be customized for population level data. However, these cut-offs can additionally or alternatively be customized by a user for performance at an individual patient level. Furthermore, if necessary, more than three levels can be created (e.g., Very High and/or Very Low as an additionally level) by the user and cut-off for each can be customized. Along the same lines, two (or more) levels (e.g., Low and Medium) can be merged to create a two-level system.

In some examples, the external monitoring device may receive a transmission of patient metric data for a number of periods, e.g., days, from the IMD, and may generate a periodic heart failure risk status (HFRS) for the periods based on the diagnostic data for the period. The external monitoring device may also differentiate the HFRS based on the maximum periodic HFRS within a lookback window prior to the current period. For example, the external monitoring device may differentiate the alerts as being either high alerts, high ongoing alerts, medium alerts and medium ongoing alerts. In some examples, the external monitoring device may differentiate HFRS as being a high HFRS, a high new HFRS, a medium HFRS and a medium new HFRS.

Such additional HFRS differentiation may assist in determining patient conditions, assessing the effectiveness of a current therapy, and determining whether therapy adjustments may be necessary. For example, during monitoring of patients, knowing whether an event is an ongoing event, not an ongoing event, a new event, or not a new event may enable more efficient treatment of patients.

In some examples, a patient with poor tissue perfusion may need to have the wrapped muscle stimulated, but a patient with good tissue perfusion, which is an indicator that the heart is in a good condition, stimulation of the wrapped may be reduced to preserve the wrapped muscle. A threshold level may indicate a level in which stimulation of the wrapped may be reduced to preserve the wrapped muscle. In some examples, circuitry 50 may be configured to reduce the number of beats that electrical therapy is delivered via the stimulating electrode(s) 62, such as decreasing a rate that heart beats are provided electrical therapy, to the wrapped muscle in response to a tissue perfusion level being above a threshold level based, at least in part, on the one or more physiologic parameters. For example, if pacing is set at every other heartbeat, circuitry 50 may adjust the electrical therapy to reduce the pacing, such as at every third beat or at every fifth beat in response to a tissue perfusion level being above a threshold level based, at least in part, on the one or more physiologic parameters. Reducing pacing rate by skipping beats may give the LD muscle increased rest, which may be helpful if the LD muscle is determined to be fatigued. In some examples, circuitry 50 may be configured to adjust the amount of electrical therapy delivered via the stimulating electrode(s) 62 to decrease stimulation of the wrapped muscle in response to a tissue perfusion level being above a threshold level based, at least in part, on the one or more physiologic parameters.

A patient's activity may be increased during the daytime and may be decreased during the nighttime. In some examples, stimulation of the wrapped muscle may be increased during daytime to correspond to increased patient activity and/or may be decreased during nighttime to correspond to decreased patient activity. This may provide enough muscle contraction to correspond to daytime activity and/or preserve the wrapped muscle during nighttime by not overstimulating the wrapped muscle at nighttime.

In some examples, circuitry 50 may be configured to adjust the amount of electrical therapy to increase stimulation of the wrapped muscle in response to determining a time of day is daytime based, at least in part, on the one or more physiologic parameter. In some examples, circuitry 50 may be configured to adjust the amount of electrical therapy to decrease stimulation of the wrapped muscle in response to determining a time of day is nighttime based, at least in part, on the one or more physiologic parameters.

In some examples, adjusting an amount of electrical therapy may include adjusting a pulse amplitude or frequency of the electrical therapy. In some examples, adjusting an amount of electrical therapy may include adding a delay and/or adjusting a duty cycle or pulse burst duration of the electrical therapy. In some examples, adjusting an amount of electrical therapy may include adjusting the electrical therapy to provide a minimum energy to capture the wrapped muscle. In some examples, a safety margin may be added to the minimum energy and the electrical therapy may be adjusted accordingly. An amount of minimum energy to capture the wrapped muscle may be checked periodically with a capture management algorithm. In some examples, adjusting an amount of electrical therapy may include adjusting one or more of a voltage, current, or pulse width of the electrical therapy. In some examples, adjusting an amount of electrical therapy may include changing a pacing rate to be delivered. In some examples, changing a pacing rate may include reducing the pacing rate by increasing an amount of heart beats that are skipped during pacing. Reducing pacing rate by skipping heart beats may give the wrapped muscle increased rest, which may be helpful when the wrapped muscle is determined to be fatigued. For example, if pacing is set at every other heartbeat, adjusting electrical therapy may include adjusting a pacing rate to a reduced rate, such as, but not limited to, every third beat or at every fifth beat. In some examples, changing a pacing rate may include increasing a pacing rate by decreasing an amount of heart beats that are skipped during pacing. For example, if pacing is set at every other heartbeat, adjusting electrical therapy may include adjusting a pacing rate to an increased rate, such as, but not limited to, two out of every three heart beats or every heartbeat.

Circuitry 50 may be configured to adjust the amount of electrical therapy to be delivered via stimulating electrode(s) 62 to adjust stimulation of the wrapped muscle in response to determining a respiration rate based, at least in part, on the one or more physiologic parameters.

Implantable medical device 10 may further include a cuff to be positioned on the phrenic nerve to sense respiration of a patient, such as respiration rate. In some examples, access may already be given to place a cuff on the phrenic nerve via the thoracotomy for a dynamic cardiomyoplasty procedure. In some examples, implantable medical device 10 may sense respiration of a patient via electrodes, such as plunge/screw electrodes, that are inserted into the diaphragm, such as being directly inserted into the diaphragm. In some examples, ICD lead 70 may sense impedance. In some examples, circuitry 50 may determine respiration of a patient, such as respiration rate, based on the sensed impedance in relation to the filling and emptying of the heart. In some examples, circuitry 50 may determine EGM drift based on one or more physiologic parameters sensed from ICD lead 70.

In some examples, heart failure patients may lose respiratory sinus arrythmia (RSA) or have a highly diminished RSA and may lose their heart rate variability as well. In an otherwise healthy individual, the heart rate is non-uniform under normal breathing. In RSA, heart rate normally increases during inspiration, and decreases during expiration. Mechanisms behind this include a lowered intrathoracic pressure during inspiration, which leads to increased venous return to the heart. This increased venous return leads to increased contractility by the Frank-Starling mechanism and increased heart rate. Additionally, there may be a slight delay between the exact phases of inspiration and expiration and the increased heart rate. When the heart is paced via a set heart rate, RSA can be lost which may contribute to sub-optimal outcomes. By determining the respiratory rate or respiratory state of the patient the pacing device may be configured to slightly increase the pacing rate during inspiration and slightly decrease the pacing rate during expiration to restore RSA. In some examples, this change in pacing rate, corresponding with restored RSA, may be on the order of about plus or minus 2 beats per minute.

In some examples, circuitry 50 may be configured to provide RSA pacing via pacing electrode(s) 74 in combination with providing stimulation of the wrapped muscles via stimulating electrode(s) to increase effectiveness of dynamic cardiomyoplasty and help restore RSA. In some examples, an ICD device, separate from IMD 10, may be used to deliver pacing, such as RSA pacing, instead of an ICD lead 70. For example, RSA pacing may be provided by one or more leadless pacemakers, such as Micra™ leadless pacemaker, available from Medtronic plc. In some examples, a leadless pacemaker, such as Micra™ may be used to deliver pacing instead of an ICD lead. In some examples, leadless pacemaker may wireless communicate with IMD 10 to coordinate delivery of RSA pacing with stimulation of the muscle wrapped around the heart.

Figure 2:
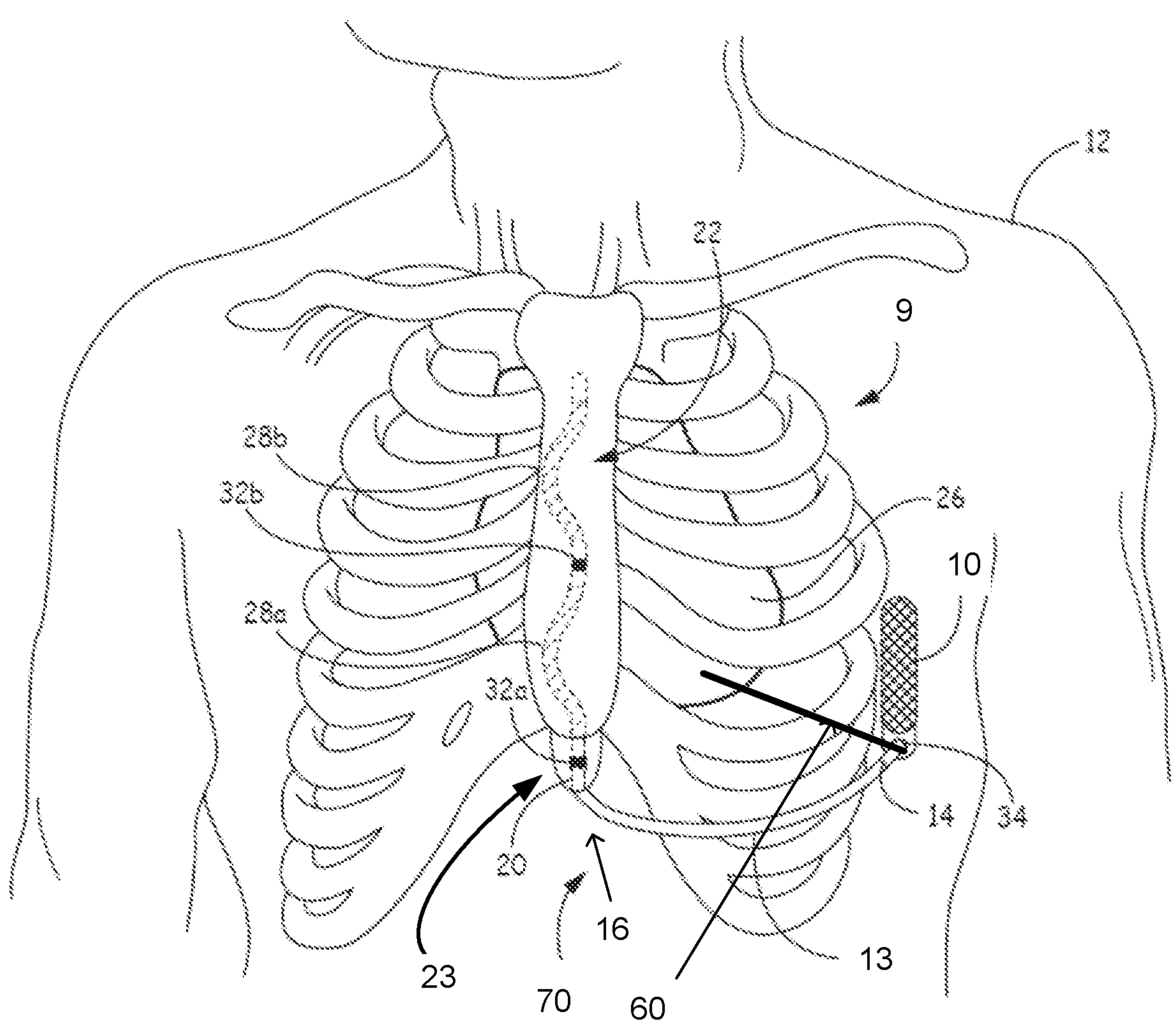
FIG. 2 is a front view of a patient implanted with the extravascular ICD system implanted intra-thoracically.

FIG. 2 is a front view of a patient 12 implanted with an extravascular ICD system 9 implanted intra-thoracically. ICD system 9 may include an IMD 10 connected to an implantable medical lead 70. ICD system 10 may further include IMD 10 connected to a stimulating lead 60 that extends from the IMD 10 to a muscle wrapped around the heart, such as the latissimus dorsi muscle graft (not shown in FIG. 2).

In some examples of dynamic cardiomyoplasty, the latissimus dorsi skeletal muscle graft may be positioned over the right ventricle and left ventricle of a patient's heart 26. The longitudinal fibers of the latissimus dorsi graft may be oriented generally parallel to the longitudinal axes of the ventricles and interventricular septum of the heart 26. The skeletal muscle may be positioned in this manner so that when it is stimulated, it compresses the ventricles, particularly the left ventricle, and improves the force of right and left ventricular contraction. In some examples, the latissimus dorsi muscle graft may be attached to the heart 26 along the borders of the ventricular walls using running sutures.

IMD 10 may include a housing that forms a hermetic seal that protects components of the IMD 10. The housing of IMD 10 may be formed of a conductive material, such as titanium or titanium alloy, which may function as a housing electrode (sometimes referred to as a can electrode). In some embodiments, IMD 10 may be formed to have or may include a plurality of electrodes on the housing. IMD 10 may also include a connector assembly (also referred to as a connector block or header) that includes electrical feedthroughs through which electrical connections are made between conductors of lead 8 and electronic components included within the housing of IMD 10. As will be described in further detail herein, the housing may house one or more processors, memories, transmitters, receivers, sensors, sensing circuitry, therapy circuitry, power sources and other appropriate components. The housing is configured to be implanted in a patient, such patient 12.

In some examples, IMD 10 may be implanted extrathoracically on the left side of the patient, e.g., under the skin and outside the ribcage (subcutaneously or submuscularly). IMD 10 may, in some instances, be implanted between the left posterior axillary line and the left anterior axillary line of the patient. IMD 10 may, however, be implanted at other extra-thoracic locations on the patient as described later.

In some examples, ICD lead 70 may include an elongated lead body 13 having a distal portion 16 sized to be implanted in an extravascular location proximate the heart, e.g., intrathoracically, as illustrated in FIG. 2, or extra-thoracically. For example, ICD lead 70 may extend extra-thoracically under the skin and outside the ribcage (e.g., subcutaneously or submuscularly) from IMD 10 toward the center of the torso of the patient, for example, toward the xiphoid process 23 of the patient. At a position proximate xiphoid process 23, the lead body 13 may bend or otherwise turn and extend superiorly. The bend may be pre-formed and/or lead body 13 may be flexible to facilitate bending.

Distal portion 16 of ICD lead 70 may reside in a substernal location such that distal portion 16 of ICD lead 70 extends superior along the posterior side of the sternum substantially within the anterior mediastinum. Anterior mediastinum may be viewed as being bounded laterally by pleurae, posteriorly by pericardium, and anteriorly by the sternum. In some instances, the anterior wall of anterior mediastinum may also be formed by the transversus thoracis and one or more costal cartilages. Anterior mediastinum includes a quantity of loose connective tissue (such as areolar tissue), adipose tissue, some lymph vessels, lymph glands, substernal musculature (e.g., transverse thoracic muscle), the thymus gland, branches of the internal thoracic artery, and the ITV.

Lead body 13 may extend superiorly extra-thoracically (instead of intra-thoracically), e.g., either subcutaneously or submuscularly above the ribcage/sternum. ICD lead 70 may be implanted at other locations, such as over the sternum, offset to the right of the sternum, angled lateral from the proximal or distal end of the sternum, or the like. In some examples, ICD lead 70 may be implanted within an extracardiac vessel within the thorax, such as the ITV, the intercostal veins, the superior epigastric vein, or the azygos, hemiazygos, and accessory hemiazygos veins. In some examples, distal portion 16 of ICD lead 70 may be oriented differently than is illustrated in FIG. 2, such as orthogonal or otherwise transverse to sternum 22 and/or inferior to heart 26. In such examples, distal portion 16 of ICD lead 70 may be at least partially within anterior mediastinum. In some examples, distal portion 16 of ICD lead 70 may be placed between the heart and lung as well as within the pleural cavity.

Lead body 13 may have a generally tubular or cylindrical shape and may define a diameter of approximately 3-9 French (Fr). However, lead bodies of less than 3 Fr and more than 9 Fr may also be utilized. In another configuration, lead body 13 may have a flat, ribbon, or paddle shape with solid, woven filament, or metal mesh structure, along at least a portion of the length of the lead body 13. In such an example, the width across lead body 13 may be between 1-3.5 mm. Other lead body designs may be used without departing from the scope of this application.

Lead body 13 may be formed from a non-conductive material, including silicone, polyurethane, fluoropolymers, mixtures thereof, and other appropriate materials, and shaped to form one or more lumens (not shown), however, the techniques are not limited to such constructions. Distal portion 16 may be fabricated to be biased in a desired configuration, or alternatively, may be manipulated by the user into the desired configuration. For example, the distal portion 16 may be composed of a malleable material such that the user can manipulate the distal portion into a desired configuration where it remains until manipulated to a different configuration.

Lead body 13 may include a proximal end 14 and a distal portion 16 which include electrodes configured to deliver electrical energy to the heart or sense electrical signals of the heart. Distal portion 16 may be anchored to a desired position within the patient, for example, substernally or subcutaneously by, for example, suturing distal portion 16 to the patient's musculature, tissue, or bone at the xiphoid process entry site. In some examples, distal portion 16 may be anchored to the patient through the use of rigid tines, prongs, barbs, clips, screws, and/or other projecting elements or flanges, disks, pliant tines, flaps, porous structures such as a mesh-like elements and metallic or non-metallic scaffolds that facilitate tissue growth for engagement, bio-adhesive surfaces, and/or any other non-piercing elements.

Distal portion 16 includes one or more defibrillation electrodes configured to deliver an anti-tachyarrhythmia, e.g., cardioversion/defibrillation, shock to heart 26 of patient 12. In some examples, distal portion 16 includes a plurality of defibrillation electrodes spaced a distance apart from each other along the length of distal portion 16. In the example illustrated by FIG. 2, distal portion 16 includes two defibrillation electrodes 28*a* and 28*b* (collectively, "defibrillation electrodes 28").

Defibrillation electrodes 28 may be disposed around or within the lead body 13 of the distal portion 16, or alternatively, may be embedded within the wall of the lead body 13. In one configuration, defibrillation electrodes 28 may be coil electrodes formed by a conductor. The conductor may be formed of one or more conductive polymers, ceramics, metal-polymer composites, semiconductors, metals or metal alloys, including but not limited to, one of a combination of the platinum, tantalum, titanium, niobium, zirconium, ruthenium, indium, gold, palladium, iron, zinc, silver, nickel, aluminum, molybdenum, stainless steel, MP35N, carbon, copper, polyaniline, polypyrrole, and other polymers. In another configuration, each of defibrillation electrodes 28 may be a flat ribbon electrode, a paddle electrode, a braided or woven electrode, a mesh electrode, a directional electrode, a patch electrode or another type of electrode configured to deliver a cardioversion/defibrillation shock to heart 26 of patient 12.

Defibrillation electrodes 28 may be electrically connected to one or more conductors, which may be disposed in the body wall of lead body 13 or in one or more insulated lumens (not shown) defined by lead body 13. In an example configuration, each of defibrillation electrodes 28 is connected to a common conductor such that a voltage may be applied simultaneously to all defibrillation electrodes 28 to deliver an anti-tachyarrhythmia shock to heart 26. In other configurations, defibrillation electrodes 28 may be attached to separate conductors such that each defibrillation electrode 28 may apply a voltage independent of the other defibrillation electrodes 28. In this case, IMD 10 or ICD lead 70 may include one or more switches or other mechanisms to electrically connect the defibrillation electrodes together to function as a common polarity electrode such that a voltage may be applied simultaneously to all defibrillation electrodes 28 in addition to being able to independently apply a voltage.

Distal portion 16 may also include one or more pacing and/or sensing electrodes configured to deliver pacing pulses to heart 26 and/or sense electrical activity of heart 26. Such electrodes may be referred to as pacing electrodes, sensing electrodes, or pace/sense electrodes. In the example illustrated by FIG. 2, distal portion 16 includes two pace/sense electrodes **32*a* and 32*b* (collectively, "pace/sense electrodes 32"). In some examples, electrodes 32 of FIG. 2 may correspond to pacing electrode(s) 74 of FIG. 1. In some examples, defibrillation electrode 28 of FIG. 2 may correspond to defibrillation electrode(s) 72 of FIG. 1**.

In the illustrated example of FIG. 2, pace/sense electrode **32*b* is positioned between defibrillation electrodes 28, e.g., within a gap between the defibrillation electrodes, and pace/sense electrode 32*a* is positioned more proximal along distal portion 16 than proximal defibrillation electrode 28*a*. In some examples, more than one electrode 32 may exist within the gap between defibrillation electrodes 28. In some examples, an electrode 32 is additionally or alternatively located distal of the distalmost defibrillation electrode 28*b***.

Electrodes 32 may be configured to deliver low-voltage electrical pulses to the heart or may sense a cardiac electrical activity, e.g., depolarization and repolarization of the heart. As such, electrodes 32 may be referred to herein as pace/sense electrodes 32. In one configuration, electrodes 32 are ring electrodes. However, in other configurations electrodes 32 may be any of a number of different types of electrodes, including ring electrodes, short coil electrodes, paddle electrodes, hemispherical electrodes, or directional electrodes. Each of electrodes 32 may be the same or different types of electrodes as others of electrodes 32. Electrodes 32 may be electrically isolated from an adjacent defibrillation electrode 28 by including an electrically insulating layer of material between electrodes 32 and adjacent defibrillation electrodes 28. Each electrode 32 may have its own separate conductor such that a voltage may be applied to or sensed via each electrode independently from another electrode 32.

Electrodes 28 are referred to as defibrillation electrodes, and electrodes 32 are referred to as pace/sense electrodes, because they may have different physical structures enabling different functionality. Defibrillation electrodes 28 may be larger, e.g., have greater surface area, than pace/sense electrodes 32 and, consequently, may be configured to deliver anti-tachyarrhythmia shocks that have relatively higher voltages than pacing pulses. The relatively smaller size of pace/sense electrodes 32 may provide advantages over defibrillation electrodes for delivering pacing pulses and sensing intrinsic cardiac activity, e.g., lower pacing capture thresholds and/or better sensed signal quality. Nevertheless, a defibrillation electrode 28 may be used to deliver pacing pulses and/or sense electrical activity of the heart, such as in combination with a pace/sense electrode 32.

Proximal end 14 of lead body 13 may include one or more connectors 34 to electrically couple ICD lead 70 to IMD 10. IMD 10 may also include a connector assembly that includes electrical feedthroughs through which electrical connections are made between the one or more connectors 34 of ICD lead 70 and the electronic components included within the housing. The housing of IMD 10 may house one or more processors, memories, transmitters, receivers, sensors, sensing circuitry, therapy circuitry, power sources (e.g., capacitors and batteries), and/or other components. The components of IMD 10 may generate and deliver electrical therapy such as anti-tachycardia pacing, cardioversion or defibrillation shocks, post-shock pacing, and/or bradycardia pacing.

In some examples, stimulating lead 60 may include an elongated lead body to be implanted in a location proximate the muscle wrapped around the heart, such as a LD muscle, e.g., intra-thoracically or extra-thoracically. Lead body of stimulating lead 60 may have a generally tubular or cylindrical shape and may define a diameter of approximately 3-9 French (Fr). However, lead bodies of less than 3 Fr and more than 9 Fr may also be utilized. In another configuration, lead body of stimulating lead 60 may have a flat, ribbon, or paddle shape with solid, woven filament, or metal mesh structure, along at least a portion of the length of the lead body 13. In such an example, the width across lead body of stimulating lead 60 may be between 1-3.5 mm. Other lead body designs may be used without departing from the scope of this application.

Lead body of stimulating lead 60 may be formed from a non-conductive material, including silicone, polyurethane, fluoropolymers, mixtures thereof, and other appropriate materials, and shaped to form one or more lumens (not shown), however, the techniques are not limited to such constructions. In some examples, lead body of stimulating lead 60 may include one or more stimulating electrodes 62 and one or more stimulating lead sensors 66 (not shown in FIG. 2).

Stimulating electrode(s) 62 may be configured to deliver electrical pulses to the muscle wrapped around the heart, such as a LD muscle. Stimulating electrode(s) 62 may be any of a number of different types of electrodes, including ring electrodes, short coil electrodes, paddle electrodes, hemispherical electrodes, or directional electrodes.

Figure 3:
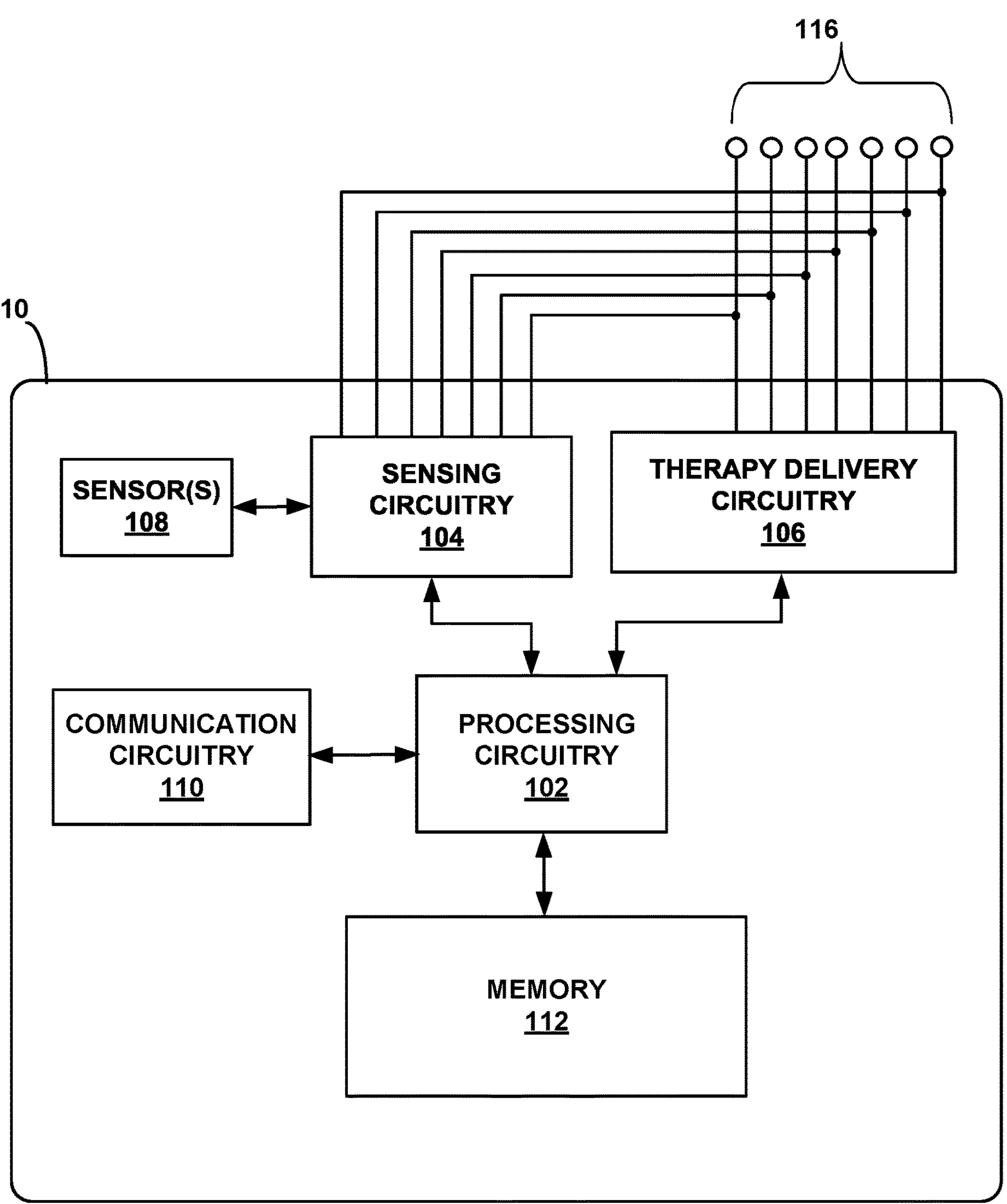
FIG. 3 is a functional block diagram of an example configuration of electronic components of an example ICD.

FIG. 3 is a functional block diagram of an example configuration of electronic components and other components of IMD 10. IMD 10 may include a processing circuitry 102, sensing circuitry 104, therapy delivery circuitry 106, sensors 108, communication circuitry 110, and memory 112. In some examples, circuitry 50, as shown in FIG. 1, may include one or more of processing circuitry 102, sensing circuitry 104, therapy delivery circuitry 106, sensors 108, communication circuitry 110. In some examples, IMD 10 may include more or fewer components. In some examples, circuitry of IMD 10 may refer to one or more of processing circuitry 102, sensing circuitry 104, therapy delivery circuitry 106, and/or communication circuitry 110. The described circuitry and other components may be implemented together on a common hardware component or separately as discrete but interoperable hardware or software components. Depiction of different features is intended to highlight different functional aspects and does not necessarily imply that such circuitry and other components must be realized by separate hardware or software components. Rather, functionality associated with one or more circuitries and components may be performed by separate hardware or software components, or integrated within common or separate hardware or software components.

Sensing circuitry 104 may be electrically coupled to some or all of electrodes 116, which may correspond to any of the defibrillation, pace/sense, and housing electrodes described herein. Sensing circuitry 104 is configured to obtain signals sensed via one or more combinations of electrodes 116 and process the obtained signals.

The components of sensing circuitry 104 may be analog components, digital components or a combination thereof. Sensing circuitry 104 may, for example, include one or more sense amplifiers, filters, rectifiers, threshold detectors, analog-to-digital converters (ADCs) or the like. Sensing circuitry 104 may convert the sensed signals to digital form and provide the digital signals to processing circuitry 102 for processing or analysis. For example, sensing circuitry 104 may amplify signals from the sensing electrodes and convert the amplified signals to multi-bit digital signals by an ADC. Sensing circuitry 104 may also compare processed signals to a threshold to detect the existence of atrial or ventricular depolarizations (e.g., P- or R waves) and indicate the existence of the atrial depolarization (e.g., P-waves) or ventricular depolarizations (e.g., R-waves) to processing circuitry 102. As shown in FIG. 3, IMD 10 may additionally include one or more sensors 108, such as one or more accelerometers, which may be configured to provide signals indicative of other parameters of a patient, such as activity or posture, to processing circuitry 102.

Processing circuitry 102 may process the signals from sensing circuitry 104 to monitor electrical activity of heart 26 of patient 12. Processing circuitry 102 may store signals obtained by sensing circuitry 104 as well as any generated EGM waveforms, marker channel data or other data derived based on the sensed signals in memory 112. Processing circuitry 102 may analyze the EGM waveforms and/or marker channel data to detect arrhythmias (e.g., bradycardia or tachycardia). In response to detecting the cardiac event, processing circuitry 102 may control therapy delivery circuitry 106 to deliver the desired therapy to treat the cardiac event, e.g., defibrillation shock, cardioversion shock, ATP, post shock pacing, or bradycardia pacing.

Therapy delivery circuitry 106 is configured to generate and deliver electrical therapy to heart 26 and/or latissimus dorsi graft 215. Therapy delivery circuitry 106 may include one or more pulse generators, capacitors, and/or other components capable of generating and/or storing energy to deliver as pacing therapy, defibrillation therapy, cardioversion therapy, cardiac resynchronization therapy, other therapy or a combination of therapies. In some instances, therapy delivery circuitry 106 may include a first set of components configured to provide pacing therapy and a second set of components configured to provide defibrillation therapy. In some instances, therapy delivery circuitry 106 may utilize the same set of components to provide both pacing and defibrillation therapy. In still other instances, therapy delivery circuitry 106 may share some of the defibrillation and pacing therapy components while using other components solely for defibrillation or pacing. Processing circuitry 102 may control therapy delivery circuitry 106 to deliver the generated therapy to heart 26 via one or more combinations of electrodes 116. and pacing therapy components while using other components solely for defibrillation or pacing. Processing circuitry 102 may control therapy delivery circuitry 106 to deliver the generated therapy to latissimus dorsi graft 215 via one or more combinations of electrodes 116. Although not shown in FIG. 3, IMD 10 may include switching circuitry configurable by processing circuitry 102 to control which of electrodes 116 is connected to therapy delivery circuitry 106 and sensing circuitry 104.

Communication circuitry 110 may include any suitable hardware, firmware, software or any combination thereof for communicating with another device, such as a clinician programmer, a patient monitoring device, a concomitant implant or the like. For example, communication circuitry 110 may include appropriate modulation, demodulation, frequency conversion, filtering, and amplifier components for transmission and reception of data with the aid of an antenna or electrode(s).

The various components of IMD 10 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Processing circuitry 102 may include fixed function circuitry and/or programmable processing circuitry. The functions attributed to processing circuitry 102 herein may be embodied as software, firmware, hardware or any combination thereof.

Memory 112 may include computer-readable instructions that, when executed by processing circuitry 102 or other components of IMD 10, cause one or more components of IMD 10 to perform various functions attributed to those components in this disclosure. Memory 112 may include any volatile, non-volatile, magnetic, optical, or electrical media, such as a random-access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

Figure 4:
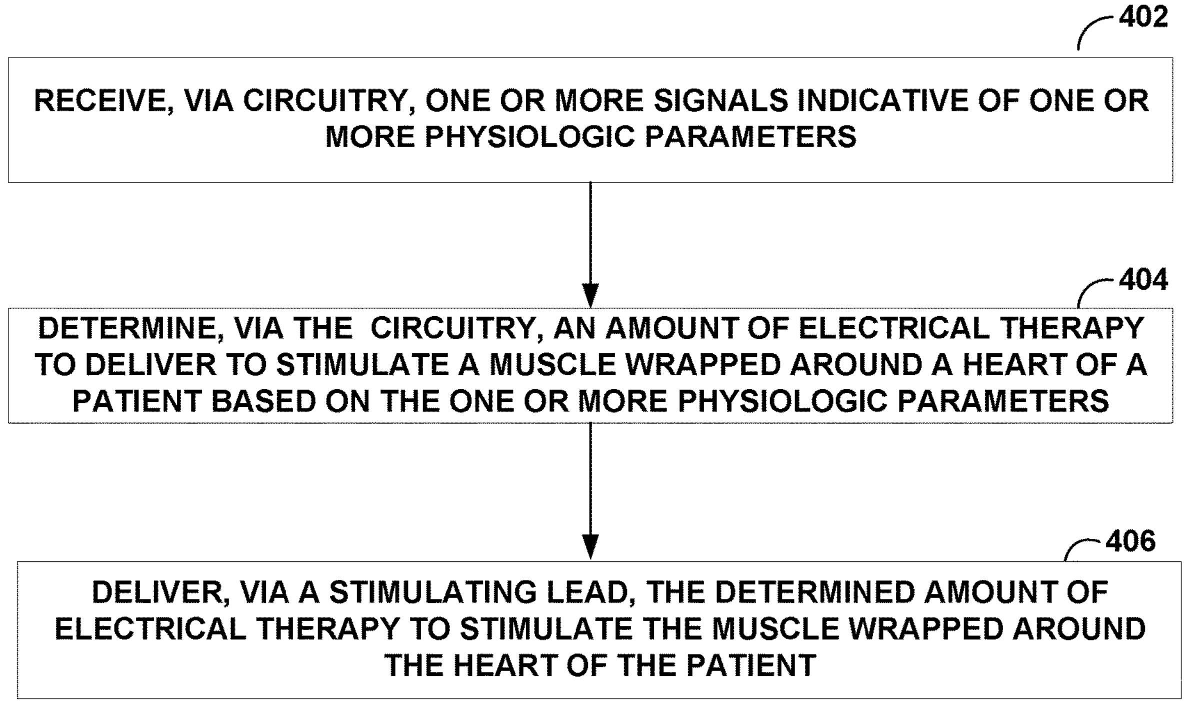
FIG. 4 is a flow diagram illustrating an example method that may be performed by one or more medical devices to deliver electrical therapy, in accordance with one or more techniques disclosed herein.

FIG. 4 illustrates an example method that may be performed by IMD 10 to deliver electrical therapy. In some examples, circuitry 50 may receive one or more signals indicative of one or more physiologic parameters (402). In some examples, circuitry 50 may determine an amount of electrical therapy to deliver to stimulate a muscle wrapped around a heart of a patient based on the one or more physiologic parameters (404). In some examples, stimulating lead 60 may deliver the determined amount of electrical therapy to simulate the muscle wrapped around the heart of the patient (406).

Figure 5:
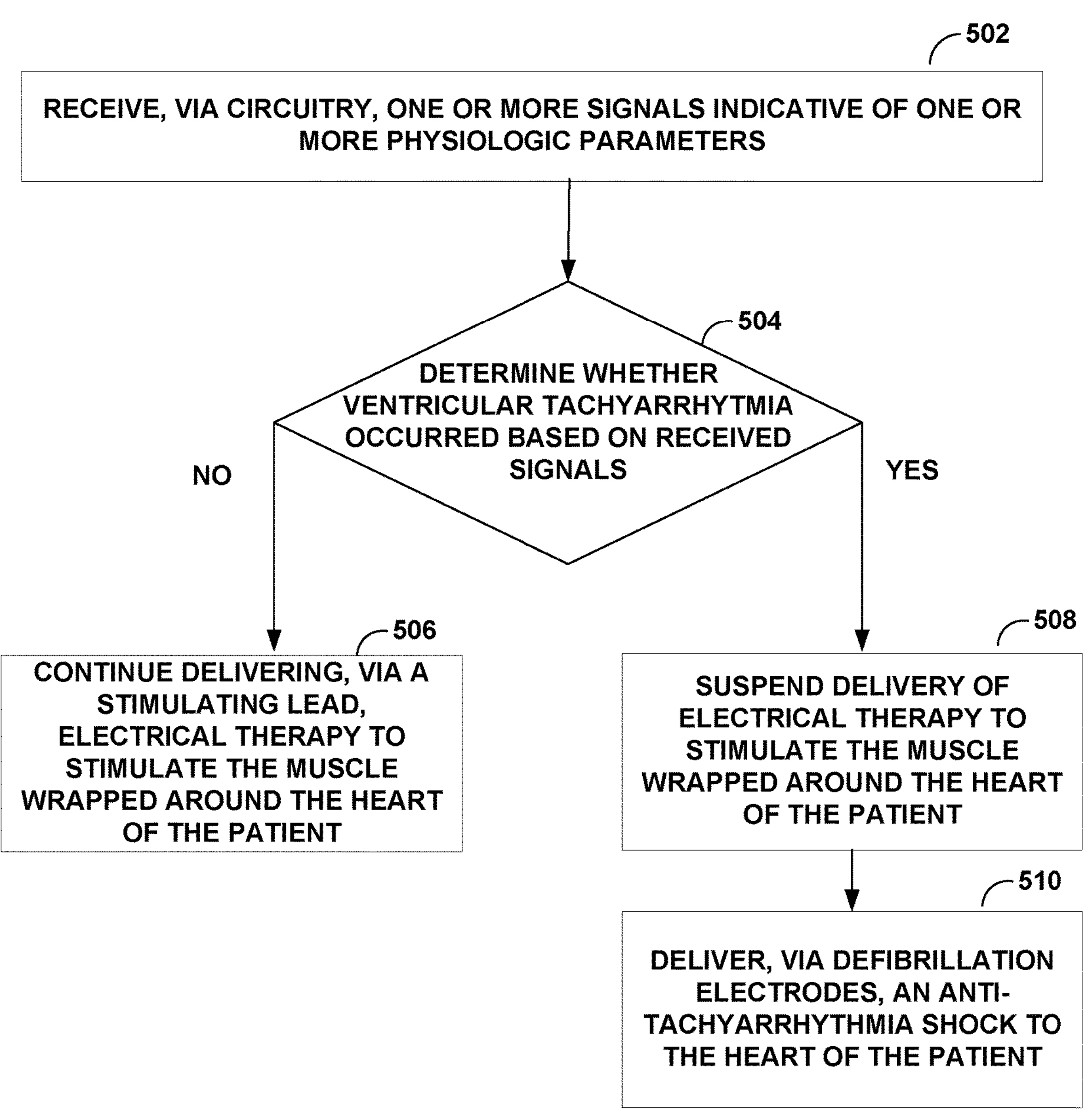
FIG. 5 is a flow diagram illustrating an example method that may be performed by one or more medical devices to adjust delivery of electrical therapy and deliver anti-tachyarrhythmia shock, in accordance with one or more techniques disclosed herein.

FIG. 5 illustrates an example method that may be performed by IMD 10 to monitor the heart, adjust delivery of electrical therapy and deliver anti-tachyarrhythmia shock. In some examples, circuitry 50 may receive one or more signals indicative of one or more physiologic parameters (502). In some examples, circuitry 50 may determine, based at least in part on the received one or more signals, whether ventricular arrhythmia occurred in a heart of the patient (504). In response to determining ventricular arrhythmia did not occur, circuitry 50 may continue providing electrical therapy to stimulate a muscle wrapped around a heart of a patient (506). In response to determining ventricular arrhythmia did occur, circuitry 50 may suspend delivery of electrical therapy to stimulate the muscle wrapped around the heart (508). In some examples, circuitry 50 may deliver, via defibrillation electrode(s) 72, an anti-tachyarrhythmia shock to the heat patient (510). Suspending delivery of electrical therapy to stimulate the muscle wrapped around the heart while an anti-tachyarrhythmia shock is delivered may reduce discomfort to the patient and/or damage to the heart, which may result in improved treatment and/or extended life of the patient.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

The following examples are illustrative of the techniques described herein.

Example 1: An implantable medical device includes a stimulating lead includes receive one or more signals indicative of one or more physiologic parameters; deliver electrical therapy to stimulate a muscle wrapped around a heart via one or more electrodes of a stimulating lead; and adjust an amount of the electrical therapy delivered, via the stimulating electrodes, based on the one or more physiologic parameters.

Example 2: The implantable medical device of example 1, wherein the circuitry is configured to receive at least one signal of the one or more signals indicative of the one or more physiological parameters via the one or more electrodes of the stimulating lead.

Example 3: The implantable medical device of any of examples 1 and 2, further includes one or more pace/sense electrodes; and one or more defibrillation electrodes, wherein the circuitry is configured to: detect a tachyarrhythmia via one or more pace/sense electrodes of the ICD lead; and based on detecting the tachyarrhythmia, deliver an antitachyarrhythmia shock via one or more defibrillation electrodes of the ICD lead.

Example 4: The implantable medical device of example 3, wherein the circuitry is configured to receive at least one signal of the one or more signals indicative of the one or more physiological parameters via at least one of: the one or more pace/sense electrodes of the ICD lead, the one or more defibrillation electrodes of the ICD lead; or one or more other sensors of the ICD lead.

Example 5: The implantable medical device of any of examples 1-4, further comprising an accelerometer positioned on the stimulating lead to detect and provide signals to the circuitry indicative of one or more physiologic parameters of the wrapped muscle, wherein the one or more signals received by are indicative of one or more physiologic parameters of the wrapped muscle, and the circuitry is configured to determine an amount of fatigue of the wrapped muscle based on the one or more physiologic parameters of the wrapped muscle.

Example 6: The implantable medical device of example 5, wherein the circuitry is configured to adjust the amount of the electrical therapy to be delivered, via the stimulating electrodes, based, at least in part, on the determined amount of fatigue of the wrapped muscle.

Example 7: The implantable medical device of any of examples 1-6, wherein the stimulating lead further includes one or more stimulating lead sensors configured to detect and provide the signals indicative of the one or more physiologic parameters.

Example 8: The implantable medical device of any of examples 1-7, wherein the physiologic parameters include one or more of time heart failure status, heart failure risk score, myocardial state, activity, muscle fatigue, tissue perfusion, contraction strength of the wrapped muscle, respiration, or posture.

Example 9: The implantable medical device of any of examples 1-8, wherein the circuitry is configured to adjust the amount of electrical therapy to increase stimulation of the wrapped muscle above an overdrive threshold in response to determining atrial fibrillation, ventricular fibrillation or ventricular tachycardia occurred based, at least in part, on the one or more physiologic parameters.

Example 10: The implantable medical device of any of examples 1-9, wherein the circuitry is configured to adjust the amount of electrical therapy to increase stimulation of the wrapped muscle in response to determining a level of activity is above a threshold value based, at least in part, on the one or more physiologic parameters.

Example 11: The implantable medical device of any of examples 1-10, wherein the circuitry is configured to adjust the amount of electrical therapy to decrease stimulation of the wrapped muscle in response to determining heart failure status is below a threshold value based, at least in part, on the one or more physiologic parameters.

Example 12, The implantable medical device of any of examples 1-11, wherein the circuitry is configured to adjust the amount of electrical therapy to decrease stimulation of the wrapped muscle in response to a tissue perfusion level being above a threshold level based, at least in part, on the one or more physiologic parameters:

Example 13: The implantable medical device of any of examples 1-12, wherein the circuitry is configured to the amount of electrical therapy based on time of day.

Example 14: The implantable medical device of any of examples 1-13, wherein the circuitry is configured to adjust the amount of electrical therapy to increase stimulation of the wrapped muscle in response to determining a time of day is daytime based, at least in part, on the one or more physiologic parameters.

Example 15: The implantable medical device of any of examples 1-14, wherein the circuitry is configured to adjust the amount of electrical therapy to decrease stimulation of the wrapped muscle in response to determining a time of day is nighttime based, at least in part, on the one or more physiologic parameters.

Example 16: The implantable medical device of any of examples 1-15, wherein the circuitry is configured to adjust the amount of electrical therapy to provide respiratory sinus arrhythmia (RSA) pacing to the wrapped muscle in response to determining a respiration rate based, at least in part, on the one or more physiologic parameters.

Example 17: An implantable medical system includes an implantable medical device includes a housing; and circuitry within the housing, the circuitry configured to: receive one or more signals indicative of one or more physiologic parameters; and output a signal to cause electrical therapy to be delivered to stimulate a muscle wrapped around a heart based on the one or more physiologic parameters; and an implantable medical lead configured to be coupled to the medical device and to receive the signal output by the circuitry, the implantable medical lead comprising one or more stimulating electrodes to deliver the electrical therapy to stimulate the muscle wrapped around the heart in response to receiving the signal received from the circuitry, wherein the circuitry is configured to send a second signal to adjust an amount of the electrical therapy to be delivered, via the stimulating electrodes, based on the one or more physiologic parameters.

Example 18: The implantable medical system of example 17, comprising the stimulating lead of any of examples 1-16.

Example 19: A method includes receiving, via circuitry, one or more signals indicative of one or more physiologic parameters; determining, via the circuitry, an amount of electrical therapy to deliver to stimulate a muscle wrapped around a heart of a patient based on the one or more physiologic parameters; and delivering, via a stimulating lead, the determined amount of electrical therapy to stimulate the muscle wrapped around the heart of the patient.

Example 20: A method for generating and delivering electrical therapy to stimulate a muscle wrapped around a heart in accordance with the medical device of any of examples 1-16.

Various examples have been described. These and other examples are within the scope of the following claims.

What is claimed is:

1. An implantable medical device comprising:
- a stimulating lead comprising one or more electrodes;
- an implantable cardioverter defibrillator (ICD) lead comprising:
  - one or more pace/sense electrodes, and
  - one or more defibrillation electrodes; and
- circuitry configured to:
  - receive one or more signals indicative of one or more physiologic parameters;
  - deliver electrical therapy to stimulate a muscle wrapped around a heart via the one or more electrodes of the stimulating lead;
  - adjust an amount of the electrical therapy delivered, via the one or more electrodes of the stimulating lead, based on the one or more physiologic parameters;
  - detect a tachyarrhythmia via one or more pace/sense electrodes of the ICD lead; and
  - based on detecting the tachyarrhythmia:
    - suspend, for a period of time, delivery of the electrical therapy to stimulate the muscle wrapped around the heart, and
    - deliver an antitachyarrhythmia shock via the one or more defibrillation electrodes of the ICD lead during the period of time.

2. The implantable medical device of claim 1, wherein the circuitry is configured to receive at least one signal of the one or more signals indicative of the one or more physiologic parameters via the one or more electrodes of the stimulating lead.

3. The implantable medical device of claim 1, wherein the circuitry is configured to receive at least one signal of the one or more signals indicative of the one or more physiologic parameters via at least one of: the one or more pace/sense electrodes of the ICD lead, the one or more defibrillation electrodes of the ICD lead; or one or more other sensors of the ICD lead.

4. The implantable medical device of claim 1, further comprising an accelerometer positioned on the stimulating lead to detect and provide signals to the circuitry indicative of one or more physiologic parameters of the wrapped muscle, wherein the one or more signals are indicative of one or more physiologic parameters of the wrapped muscle, and the circuitry is configured to determine an amount of fatigue of the wrapped muscle based on the one or more physiologic parameters of the wrapped muscle.

5. The implantable medical device of claim 4, wherein the circuitry is configured to adjust the amount of the electrical therapy to be delivered, via the one or more electrodes of the stimulating lead, based, at least in part, on the determined amount of fatigue of the wrapped muscle.

6. The implantable medical device of claim 1, wherein the stimulating lead further includes one or more stimulating lead sensors configured to detect and provide the one or more signals indicative of the one or more physiologic parameters.

7. The implantable medical device of claim 1, wherein the one or more physiologic parameters include one or more of time, heart failure status, heart failure risk score, myocardial state, activity, muscle fatigue, tissue perfusion, contraction strength of the wrapped muscle, respiration, or posture.

8. The implantable medical device of claim 1, wherein the circuitry is configured to adjust the amount of electrical therapy to increase stimulation of the wrapped muscle above an overdrive threshold in response to determining atrial fibrillation, ventricular fibrillation or ventricular tachycardia occurred based, at least in part, on the one or more physiologic parameters.

9. The implantable medical device of claim 1, wherein the circuitry is configured to adjust the amount of electrical therapy to increase stimulation of the wrapped muscle in response to determining a level of activity is above a threshold value based, at least in part, on the one or more physiologic parameters.

10. The implantable medical device of claim 1, wherein the circuitry is configured to adjust the amount of electrical therapy to decrease stimulation of the wrapped muscle in response to determining heart failure status is below a threshold value based, at least in part, on the one or more physiologic parameters.

11. The implantable medical device of claim 1, wherein the circuitry is configured to adjust the amount of electrical therapy to decrease stimulation of the wrapped muscle in response to a tissue perfusion level being above a threshold level based, at least in part, on the one or more physiologic parameters.

12. The implantable medical device of claim 1, wherein the circuitry is configured to adjust the amount of electrical therapy based on time of day.

13. The implantable medical device of claim 1, wherein the circuitry is configured to adjust the amount of electrical therapy to increase stimulation of the wrapped muscle in response to determining a time of day is daytime based, at least in part, on the one or more physiologic parameters.

14. The implantable medical device of claim 1, wherein the circuitry is configured to adjust the amount of electrical therapy to decrease stimulation of the wrapped muscle in response to determining a time of day is nighttime based, at least in part, on the one or more physiologic parameters.

15. The implantable medical device of claim 1, wherein the circuitry is configured to adjust the amount of electrical therapy to provide respiratory sinus arrhythmia (RSA) pacing to the wrapped muscle in response to determining a respiration rate based, at least in part, on the one or more physiologic parameters.

16. An implantable medical system comprising:
- an implantable medical device comprising:
  - a housing; and
  - circuitry within the housing, the circuitry configured to:
    - receive one or more signals indicative of one or more physiologic parameters; and
    - output a signal to cause electrical therapy to be delivered to stimulate a muscle wrapped around a heart based on the one or more physiologic parameters; and
- an implantable medical lead configured to be coupled to the medical device and to receive the signal output by the circuitry, the implantable medical lead comprising one or more electrodes to deliver the electrical therapy to stimulate the muscle wrapped around the heart in response to receiving the signal received from the circuitry; and
- an implantable cardioverter defibrillator (ICD) lead comprising one or more pace/sense electrodes and one or more defibrillation electrodes,
- wherein the circuitry is configured to:
  - send a second signal to adjust an amount of the electrical therapy to be delivered, via the one or more electrodes of the implantable medical lead, based on the one or more physiologic parameters;
  - detect a tachyarrhythmia based on a signal received via the one or more pace/sense electrodes of the ICD lead;
  - based on the detection of the tachyarrhythmia:
    - suspend, for a period of time, delivery of the electrical therapy to stimulate the muscle wrapped around the heart, and
    - deliver an antitachyarrhythmia shock via the one or more defibrillation electrodes of the ICD lead during the period of time.

17. The implantable medical system of claim 16, further comprising an accelerometer positioned on the medical lead to detect and provide signals to the circuitry indicative of one or more physiologic parameters of the wrapped muscle,
- wherein the one or more signals received by the circuitry are indicative of one or more physiologic parameters of the wrapped muscle, and the circuitry is configured to determine an amount of fatigue of the wrapped muscle based on the one or more physiologic parameters of the wrapped muscle, and wherein the circuitry is configured to adjust the amount of the electrical therapy to be delivered, via the one or more electrodes of the implantable medical lead, based, at least in part, on the determined amount of fatigue of the wrapped muscle.

18. A method comprising:
- receiving, via circuitry, one or more signals indicative of one or more physiologic parameters;
- determining, via the circuitry, an amount of electrical therapy to deliver to stimulate a muscle wrapped around a heart of a patient based on the one or more physiologic parameters;
- delivering, via a stimulating lead, the determined amount of electrical therapy to stimulate the muscle wrapped around the heart of the patient;
- receiving, via one or more pace/sense electrodes of an implantable cardioverter defibrillator (ICD) lead, one or more sensed signals indicative of tachyarrhythmia;
- detecting, based on the one or more sensed signals indicative of tachyarrhythmia, a tachyarrhythmia;
- based on detecting the tachyarrhythmia:
  - suspending, for a period of time, delivery of the electrical therapy to stimulate the muscle wrapped around the heart, and
  - delivering, via one or more defibrillation electrodes of the ICD lead, an antitachyarrhythmia shock during the period of time.

19. The method of claim 18, further comprising determining, via the circuitry, an amount of fatigue of the wrapped muscle based on the one or more physiologic parameters, and adjusting the amount of the electrical therapy to be delivered based, at least in part, on the determined amount of fatigue of the wrapped muscle.

* * * * *